United States Patent [19]

Kitajima et al.

[11] 4,337,222
[45] Jun. 29, 1982

[54] HEMOGLOBIN CONCENTRATION DETERMINING ARTICLE

[75] Inventors: Masao Kitajima; Fuminori Arai; Asaji Kondo, all of Asaka, Japan

[73] Assignee: Fuji Photo Film Co., Ltd., Kanagawa, Japan

[21] Appl. No.: 223,062

[22] Filed: Jan. 7, 1981

[30] Foreign Application Priority Data

Jan. 7, 1980 [JP] Japan ................................. 55-435

[51] Int. Cl.³ ............................................ G01N 33/72
[52] U.S. Cl. ...................................................... 422/56
[58] Field of Search ............................................ 422/56

[56] References Cited

U.S. PATENT DOCUMENTS 4,250,257 2/1981 Lee ........................................ 422/56

*Primary Examiner*—Sidney Marantz
*Attorney, Agent, or Firm*—Sughrue, Mion, Zinn, Macpeak & Seas

[57] ABSTRACT

A hemoglobin concentration-determining article comprising a water-impermeable support having integrally provided thereon, in sequence, a hydrophilic binder layer and a porous spreading layer which has a hydrophilic surface and in which the surface of the internal voids or the interior is hydrophilic and water-insoluble, said porous spreading layer being constituted so that an aqueous sample applied thereto can be spread and incorporated therein in a substantially definite volume per unit area.

11 Claims, 3 Drawing Figures

Hb LEVEL (g/dl)

HEMOGLOBIN CONCENTRATION DETERMINING ARTICLE

BACKGROUND OF THE INVENTION

1. Field of the Invention

This invention relates to a multilayered hemoglobin concentration-determining material for determining the hemoglobin concentration in aqueous solutions, especially blood hemoglobin concentration, which is an important test item in the field of medical, clinical or physiological hematology.

2. Development of the Invention

As is well known, blood is composed of plasma and cell components (e.g., erythrocytes, leukocytes, thrombocytes, etc.).

The concentration of hemoglobin in whole blood is a particularly important analytical item in hematology as well as the number of erythrocytes and hematocrit.

As one method for determining the hemoglobin concentration in aqueous solutions, e.g., blood (hereinafter abbreviated Hb), there is known the method of measuring the absorbance of a definite volume of hemolytic or non-hemolytic dilutions and calculating the Hb concentration based on the thus obtained data. However, this conventional method has the defects that it requires a long time and complicated wet procedures.

Another method of determining the blood hemoglobin concentration uses a dry sheet and is known as the Tallqvist method (T. W. Tallqvist, *Z. Klin. Med.*, 40, 137, 1900). This method involves saturating a water-absorbing paper (e.g., filter paper) with a blood sample, and measuring the reflective optical density thereof.

Japanese Pat. application (OPI) No. 143885/77 (corresponding to U.S. Pat. No. 4,057,394) discloses a modified Tallqvist method of determining the blood hemoglobin concentration using a sheet-like material (the term "OPI" as used herein refers to a "published unexamined Japanese patent application"). This method involves preparing a blood-absorbing matrix by impregnating a porous medium such as a filter paper or textile with particles having a high refractive index, such as titanium oxide particles, saturating this matrix with a blood sample, and measuring the reflectivity thereof. This patent specification also describes a method of using the matrix adhesively laminated to a hydrophobic carrier like a polyester film. It is clear, however, that in such cases means for releasing and removing air contained in the blood matrix are necessary to attain good accuracy.

This specification further gives an experimental example relating to an Hb concentration-determining method using a multilayered analytical element as described in DT-OS No. 2,882,760, which element is formed by coating an enzyme- and color reagent-containing gelatin layer on a film base, then coating thereon a cellulose acetate layer containing dispersed therein titanium dioxide fine particles, further coating thereon a cellulose acetate layer containing diatomaceous earth and salicyclic acid, followed by drying. A blood sample is applied to the upper surface of the thus formed multilayered product to saturate the same and reflectivity is measured from above the upper surface thereof using a reflective spectrograph, the blood hemoglobin concentration thus being determined.

The two above-described methods relate to applying a blood sample to a porous membrane containing light-scattering particles such as titanium oxide particles, and measuring reflective optical density from the blood sample-applied side.

SUMMARY OF THE INVENTION

The hemoglobin concentration-determining material of the present invention is a material for determining the Hb in aqueous solutions which has a hydrophilic, porous spreading layer which does not contain any light-scattering particles in a hydrophilic binder layer.

One object of the present invention is to provide a simple, dry type material which permits one to determine the hemoglobin concentration only by essentially dry procedure of applying thereto an extremely small amount of aqueous solution sample, e.g., whole blood.

The hemoglobin concentration-determining material in accordance with this invention is useful for determining the hemoglobin concentration in aqueous solutions such as blood, occult blood in spinal fluid, etc., especially blood.

The present hemoglobin concentration-determining material comprises a water-impermeable support having provided thereon, in sequence, a hydrophilic binder layer and a porous spreading layer which has a hydrophilic surface and in which the surface of the internal voids or the interior is hydrophilic and water-insoluble (hereinafter merely referred to as hydrophilic porous spreading layer), the porous spreading layer being constituted so that an aqueous solution sample, e.g., a blood sample, applied thereto is spread and incorporated therein in a substantially definite volume per unit area.

BRIEF DESCRIPTION OF THE DRAWINGS

In FIGS. 1 and 2, numeral 1 designates a water-impermeable support, 2 a hydrophilic binder, 3 a hydrophilic porous spreading layer, 4 a spread circle, arrow A the direction of applying an aqueous solution sample and viewing and measuring the spread circle from the porous spreading layer side, and arrow B the direction of viewing and measuring the spread circle from the support side in the case of using a transparent water-impermeable support.

DESCRIPTION OF THE PREFERRED EMBODIMENTS

The present invention will be described by reference to an Hb concentration-determining sheet shown in the attached drawings, which represent one embodiment of the present invention.

Figure 1:
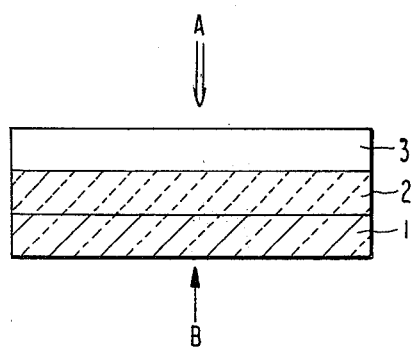
FIG. 1 is a schematic sectional view showing one embodiment of an Hb concentration-determining material of the present invention.

The Hb concentration-determining sheet of the present invention has a fundamental structure as shown in FIG. 1 wherein a hydrophilic binder layer 2 and a hydrophilic porous spreading layer 3 are provided in sequence on a water-impermeable plane support 1 to form an integral sheet.

Figure 2:
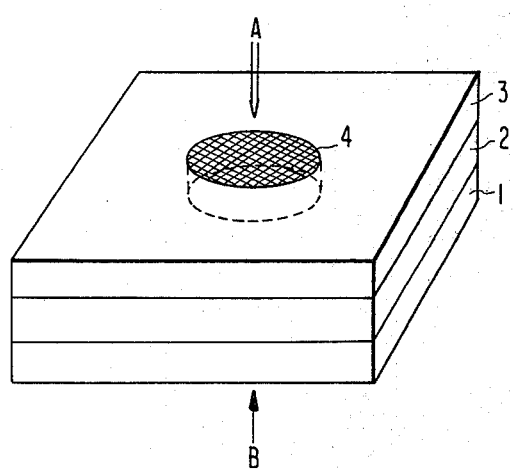
FIG. 2 is a perspective view showing the spread state of an aqueous solution sample applied to the hydrophilic porous spreading layer of the Hb concentration-determining sheet shown in FIG. 1.

In determining the Hb concentration, a drop of an aqueous solution sample such as blood (e.g., whole blood, a hemolytic solution or diluted blood) is applied to the hydrophilic porous spreading layer as indicated by arrow A as shown in FIG. 1 and FIG. 2, the latter showing a perspective view of the Hb concentration-determining sheet of the present invention.

The invention will be hereinafter explained with reference to the blood sample, but it is not to be construed that the invention is limited thereto.

The amount of blood sample applied is suitably between about 5 $\mu$l and 100 $\mu$l, for example, 10 $\mu$l.

The thus applied blood sample immediately spreads into the hydrophilic porous spreading layer in the horizontal direction to form a red spread circle and a concentric erythrocyte-free circle of a slightly larger diameter therearound within one second to several ten seconds.

Hb concentration is determined by measuring the transmission or reflection optical density of the red spread circle as shown in FIG. 2 from the direction indicated by arrow A or B. The Hb concentration can immediately be determined by converting the optical density to Hb concentration using a previously prepared conversion table or calibration.

The present invention also includes a method of determing the Hb concentration using a sheet-like material comprising a water-impermeable plane support having provided thereon a hydrophilic binder layer and a hydrophilic porous spreading layer in a fluid contact state through the procedure of coating or lamination, which state is defined in U.S. Pat. Nos. 3,922,158 and 4,042,335 and U.S. Pat. No. Re. 30,267.

The constituents constituting the Hb concentration of the present invention will now be described below in more detail.

As the hydrophilic porous spreading layer, there can be used a fibrous or non-fibrous porous membrane which has a hydrophilic surface and in which the surface of the internal voids or the interior is hydrophilic and water-insoluble.

The degree of porosity thereof varies depending upon the degree of hydrophilicity, the state of the pores, the form and distribution of the pores, etc., and no general range can be given. By way of general guidance, however, where the spreading layer comprises a non-fibrous porous material, the mean pore diameter is in the range of from about 2.5 $\mu$m to about 500 $\mu$m, preferably from about 3 $\mu$m to about 100 $\mu$m and, where it comprises a fibrous porous material such as a textile (broad cloth), textiles formed using two folded yarns of about 40 to about 100, preferably from about 60 to about 80, yarn number count are used. A suitable degree of porosity ranges from about 20 to 80%, preferably from about 25 to 80%. Additionally, in the case of using textiles, the size range of texture or mesh was examined to find that the diameter of the open pores of texture itself might be up to about 1 mm for the hydrophilic porous spreading layer.

As such hydrophilic porous spreading layer, there can be used non-fibrous porous membranes such as a membrane filter as disclosed in Japanese Patent Publication No. 2999/73 (corresponding to U.S. Pat. Nos. 3,553,067 and 3,594,263), Japanese Pat. application (OPI) Nos. 53888/74 (corresponding to U.S. Pat. No. 3,922,158) and 131786/77 (corresponding to U.S. Pat. No. 4,050,898), etc., or those prepared by making the membrane filter hydrophilic, or porous powder membranes, hydrophilic textiles as described in Japanese Patent Application No. 72047/79 (corresponding to U.S. patent application Ser. No. 157,737, filed June 9, 1980), sheets composed of glass fibers or papers, etc. Exemplary fabrics which can be used may be knitted or woven, and suitable examples of fabrics which can be used include fabrics composed of natural fibers, fabrics of mixed yarns or natural fibers and synthetic polymers, and fabrics composed of synthetic polymers. Of these, hydrophilic textiles (hydrophilicity is typically imparted thereto) having the characteristics hereinafter described are particularly preferable. When using membrane filters, those with a pore size of from about 3 $\mu$m to about 500 $\mu$m can be used, with a pore size from about 3 $\mu$m to about 100 $\mu$m being more preferred. The thickness of the porous spreading layer is not particularly limited as long as it is not less than 10 $\mu$m but, in view of the amount of applied sample, measuring accuracy, handling ease, etc., it is preferably in the range of from about 30 $\mu$m to about 3 mm, more preferably from about 50 $\mu$m to about 1 mm, and most preferably from about 100 $\mu$m to about 500 $\mu$m.

The hydrophilic porous spreading layer used in the present invention may have a uniform structure composed of a single material or may be formed by combining two or more materials having different physical properties to obtain improved properties as will be hereinafter described.

As the process for integrally providing a hydrophilic porous spreading layer on a binder layer to be described hereinafter, one can integrally laminate a previously prepared porous membrane or textile to the binder layer or coat a solution or dispersion capable of forming the hydrophilic porous spreading layer on the binder layer to thereby integrally form a porous spreading layer.

The hydrophilic porous spreading layer used for the Hb concentration-determining sheet of the present invention has such properties that the surface to which the sample is to be applied and the surface of voids in the hydrophilic porous spreading layer or the interior thereof have high hydrophilicity so that when a drop of the sample is applied thereto the sample is spread substantially isotropically within the plane of sample application.

In order to obtain such properties, the porous materials used must be subjected treatment to render them hydrophilic. As such treatments, there can be used adsorption using a hydrophilic compound such as a cationic, anionic, or nonionic surfactant or a plasticizer, or a colloid (e.g., gelatin); hydrolysis with an acid or an alkali; reaction with a hydrophilic compound; corona treatment; flame treatment; ultraviolet light irradiation; electric discharge; vacuum deposition; spraying; etc.

Addition of agents to stabilize the hue of hemoglobin, such as a pH buffer, an anticoagulant, an antihemolytic agent, an antioxidant, an oxidizing agent, etc., and erythrocyte membrane-modifying agents such as a dye, a pigment, an inorganic salt, an aldehyde, an isocyanate, hydrogen peroxide, etc., to the hydrophilic porous spreading layer serve to improve accuracy or to improve procedures such as readout.

In order to uniformly spread whole blood, a hydrophilic porous spreading layer having a particularly good spreading properties is necessary. A double layer hydrophilic porous spreading layer comprising an upper layer composed of a textile or mesh having excellent spreading properties and a lower porous layer having small pores such as a hydrophilicity-imparted membrane filter exhibits excellent capability of uniformly and finely spreading such a blood sample.

In the Hb concentration-determining sheet of the present invention, the aqueous component and water-soluble ingredients of an aqueous solution sample uniformly spread within the hydrophilic porous spreading layer permeate in a state of being uniformly spread in the underlying hydrophilic binder layer, and hence the porous spreading layer is never saturated with an aqueous solution sample. One reason for this is that the hydrophilic porous spreading layer has a function of uniformly spreading an aqueous solution sample with leaving at least about 10% (by volume) of void upon uniform spreading of the sample. Therefore, the material of the present invention does not result in the disadvantageous phenomenon of forming fine aerial cells upon saturation of the porous spreading layer with an aqueous solution sample, and thus it is not necessary to particularly provide air-permeation means in the hydrophilic porous spreading layer and/or the hydrophilic binder layer. These points clearly differentiate the present invention from the testing element described in the aforesaid Japanese Patent Application (OPI) No. 143885/77.

As the hydrophilic binder to be used for the hydrophilic binder layer, there can be used a wide variety of materials such as natural hydrophilic high molecular weight materials (e.g., gelatin, agarose, dextran, etc.) and hydrophilic synthetic high molecular weight materials (e.g., polyvinyl alcohol, polyacrylamide, polyacrylic acid, etc.). Of these, gelatin for photographic use is most preferred due to its excellent swelling properties in water, gel-forming capability, adhesion properties, water-absorbing properties, etc., and good producibility.

Various additives may be added to the hydrophilic binder layer for the purpose of stabilizing the hue of hemoglobin and preventing penetration, diffusion or precipitation of hemoglobin as well as controlling spreading. As such additives, there can be illustrated low or high molecular weight materials such as nonionic, cationic, or anionic surfactants, plasticizers, inorganic salts, organic acid salts, pH buffers, pigments, dyes, solid fine particulate fibers, oxidizing agents, reducing agents, acids, alkalis, etc.

For the purpose of facilitating readout of the diameter of red spread circle, there may be added a pH indicator which acquires or loses color depending upon the pH of the blood serum, or a color reagent which reacts with a blood serum ingredient such as albumin to acquire color, such as Bromocresol Green.

The hydrophilic binder layer may in some cases be formed of two or more sub-layers for the purpose of improving adhesion and ease of readout and preventing curling.

The thickness of the binder layer ranges from about 0.1 $\mu$m to 1 mm, preferably from 1 $\mu$m to 100 $\mu$m, particularly preferably from 5 $\mu$m to 50 $\mu$m.

Of the materials for forming the Hb concentration-determining sheet of the present invention, the water-impermeable plane support is formed using a plate-like transparent or semitransparent material such as glass, a synthetic resin film such as a polyester (e.g., polyethylene terephthalate, bisphenol A polycarbonate, etc.), a cellulose ester (e.g., cellulose diacetate, cellulose triacetate, cellulose acetate propionate, etc.), polymethyl methacrylate or the like. The thickness of the support ranges from about 10 $\mu$m to about 3 mm, preferably from about 20 $\mu$m to about 1 mm, most preferably from about 50 $\mu$m to about 500 $\mu$m.

Rigid plate-like supports such as glass or plastic plates may be used for some end uses but, in many cases, flexible films are advantageous in producibility and ease in handling. It is of course possible to use, if desired or necessary, in combination with other transparent or opaque support according to the use and storage conditions.

When a small amount (e.g., 10 $\mu$l) of a non-diluted or diluted sample (for example, whole blood, diluted whole blood, etc.) is applied to a hydrophilic porous spreading layer of the Hb concentration-determining sheet of the present invention, the sample is rapidly spread within the hydrophilic porous spreading layer uniformly in a flat manner (i.e., in such a manner that a substantially definite volume of the sample is incorporated per unit area). At this time, a hydrophilic binder layer lying under the porous spreading layer absorbs moisture and low molecular weight diffusible substances dissolved therein, and hence prevents the formation of fine aerial cells during the spreading of the sample which would make the spreading non-uniform, thus serving to spread the sample rapidly and uniformly within the hydrophilic porous spreading layer.

In addition, the hydrophilic binder layer will not allow proteins such as albumin and globulin and hemolytic hemoglobin as well as solid ingredients such as erythrocytes, leukocytes, thrombocytes, etc., to permeate due to its semipermeable properties. Therefore, the hemoglobin concentration to be measured is uniformly spread at the interface between the hydrophilic binder layer and the porous spreading layer in a flat manner. Thus, the surface at which optical reflection density is to be measured is not uneven but rather is flat, leading to high accuracy in the measurement.

Another important function of the hydrophilic binder layer is to stabilize hemoglobin. As is well known, hemoglobin is easily oxidized when dried or in contact with air, resulting in a change in its hue or a change in its absorption wavelength. Therefore, in order to accurately measure the amount of hemoglobin in a solution, it is necessary to stabilize the absorption spectrum of hemoglobin itself. For this purpose, the measurement is conducted by converting hemoglobin to, for example, cyanmetohemoglobin.

The Hb concentration-determining sheet of the present invention also permits one to measure optical density from the sample-applied side similarly with the aforesaid known techniques. In such cases, however, changes in the degree of drying of the sheet surface, oxidation or denaturation of hemoglobin, etc., are so serious that inaccurate data results.

On the other hand, when optical density is measured (after application of a blood sample) from the side opposite the sample-applied side, or from the hydrophilic binder side through a transparent support, denaturation of hemoglobin at the measurement face and the influence of drying are much less than at the sample-applied surface; thus, measurement of an extremely stable interface of high accuracy is obtained.

Another advantage of the method of measuring optical density through the transparent support of the Hb concentration-determining sheet of the present invention is to expand the Hb concentration range where measurement of the Hb concentration is possible. That is, when optical density is measured from the sample-applied side—similar to the case of using the Hb concentration-determining sheet described in Japanese Patent Application (OPI) No. 143885/77—a high proportion of erythrocytes exist on the sample-applied surface and, as a result, the optical surface reflection density becomes so high that, in the case of using, e.g., blood of a high hemoglobin content, optical surface reflection density reaches saturation, thus rendering quantitative measurement impossible. In contrast, when measuring from the side opposite the sample-applied side through a transparent support and a hydrophilic binder layer, erythrocytes do not aggregate to form a layer on the measured face and only the amount of sample diffused onto the hydrophilic binder layer is measured. Hence, saturation of reflective optical density takes place only under extreme circumstance. Thus, measurement of optical density from the side opposite the sample-applied side remarkably expands the Hb concentration range where the Hb concentration can be determined.

The Hb concentration-determining sheet of the present invention also provides a method of determining Hb concentration by merely applying thereto a drop of an aqueous solution sample and measuring the optical density of a circle formed on the sheet. The principle of the present invention will be further outlined below.

The hydrophilic porous spreading layer used in the present invention comprises a hydrophilic porous material which is constituted so that a sample can be uniformly spread in a substantially definite volume per unit area without being influenced by the amount or viscosity of the liquid sample or blood sample, i.e., by the amounts of hematocytes or proteins in the blood. Therefore, the Hb concentration can immediately be obtained by applying a drop of an aqueous solution sample to the sheet and directly measuring the Hb density, after completion of the spreading, using, e.g., red light.

One most characteristic aspect of the Hb concentration-determining sheet of the present invention is that the Hb concentration can be determined without accurately weighing a sample. Incidentally, blood has a high viscosity and is liable to undergo changes such as hemolysis due to changes in temperature, contact with air, mechanical vibration, etc., and hence weighing of a blood sample itself is difficult. The Hb concentration-determining sheet of the present invention eliminates the necessity of accurately weighing an aqueous solution sample and, in addition, enables one to determine the Hb concentration using a sample which has undergone some hemolysis in the same manner as with a fresh sample.

The Hb concentration-determining sheet of the present invention may be used as a small piece such as a strip or a chip suited for one measurement, or may be used in a sheet form permitting one to determine the Hb concentration of a plurality of samples. Further, it may be utilized in a roll form which is convenient for continuous measurement.

The present invention will now be described in more detail by reference to examples of preferred embodiments of the present invention which, however, do not limit the present invention in any way.

EXAMPLE 1

A gelatin layer was coated on a 185 μm thick transparent polyethylene terephthalate (PET) film subbed for gelatin in a dry thickness of 15 μm and dried. A microfilter (porous spreading layer composed of cellulose triacetate, FM-500, made by Fuji Photo Film Co., Ltd.) of a 5 μm mean pore size impregnated with 0.5% (by weight) alkylphenoxypolyethoxyethanol (surfactant, Triton X-405, made by Rohm & Haas Co.) was press-laminated on the gelatin layer under swelling with water to prepare an Hb concentration-determining sheet (multilayered film).

Fresh ACD preserved blood (preserved blood containing as preserving agents sodium citrate, citric acid and dextrose) for transfusion was centrifuged to separate the same into a hemocyte component and a blood serum component which were then mixed with each other at various ratios to prepare a series of known samples having a hematocrit content of from 0 to 70%. Diluted hemolytic solutions were prepared for respective samples, and the Hb concentration of each solution determined by measuring absorbency of the solution. The Hb concentration was thus found to be 0 to 24.7 mg/dl.

Separately, 10 μl of each sample blood having corresponding Hb concentration was applied to the hydrophilic porous spreading layer of the Hb concentration-determining sheet prepared according to the aforesaid process. The blood samples were spread in a circular form of a substantially definite area irrespective of the Hb concentration.

Figure 3:
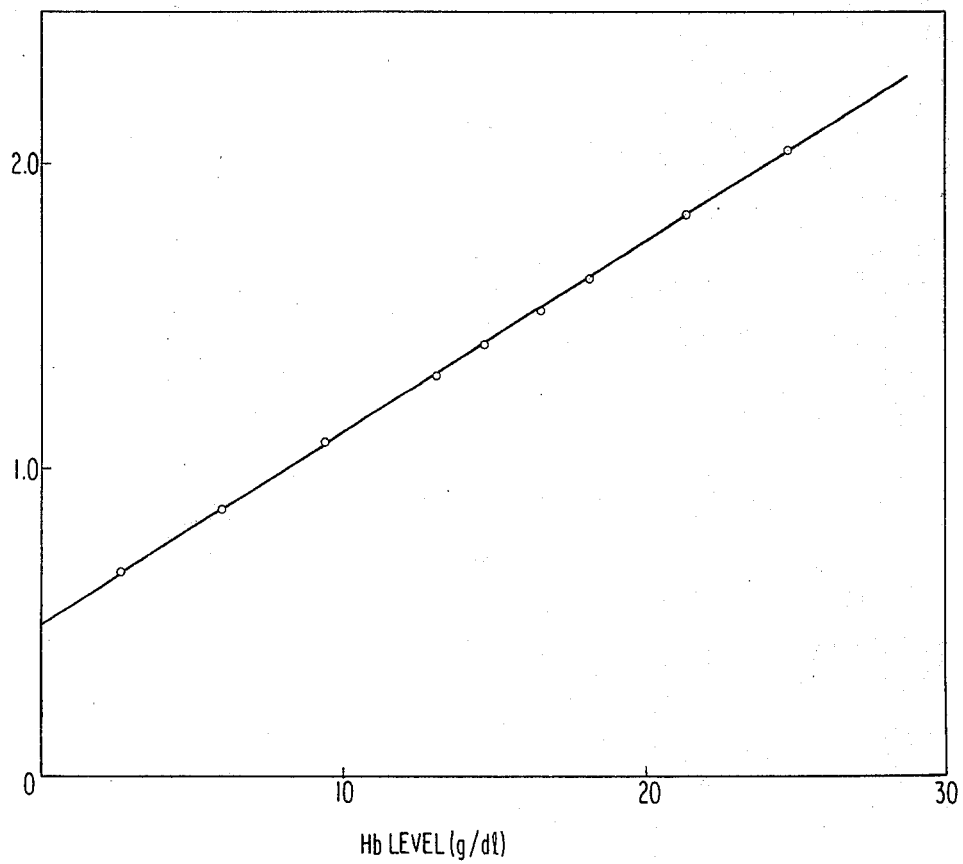
FIG. 3 is a graph showing the relationship between the Hb concentration determined according to standard method and reflective optical density measured using the Hb concentration-determining sheet of the present invention.

One minute after application, the red light reflection optical density of the sample-spread porous portion was determined from the transparent PET film side using a Macbeth reflection optical densitometer (RD-514). The relation between the Hb concentration of the respective blood samples and the reflective optical density was as shown in FIG. 3, thus they showed a good correlation with each other.

EXAMPLE 2

Hb concentration-determining sheets were prepared using as a hydrophilic porous spreading layer a cloth (10% cotton; formed by using two folded yarns of 80 yarn number count) obtained by impregnating the same with water containing 0.2% polyoxyethylene nonylphenoxy ether (nonionic surfactant, HS210, made by Nippon Oils & Fats Co., Ltd.) in place of the microfilter used in Example 1.

The relation between Hb concentration and reflective optical density (measured by means of a Macbeth RD514) was examined in the same manner as in Example 1 using the thus prepared Hb concentration-determining sheets. For purpose of comparison, optical density data obtained by measuring from the sample-applied side (the side of porous spreading layer) were compared to the data obtained by measuring from the transparent PET film side. As is shown in Table 1, data obtained from the transparent PET support side were remarkably better than that from the porous spreading layer side.

TABLE 1

| | Hb Concentration Determined According to Standard Method | | | | | |
|---|---|---|---|---|---|---|
| | 2.5 | 6.3 | 11.7 | 17.4 | 20.3 | 22.8 |
| Reflective Optical Density Measured from Transparent PET Film Side | 0.71 | 0.87 | 1.06 | 1.39 | 1.51 | 1.62 |
| Reflective Optical Density Measured from Porous Spreading Layer Side | 0.66 | 1.02 | 1.38 | 1.71 | 1.73 | 1.71 |

EXAMPLE 3

Photographic gelatin containing 0.1% nonionic surfactant, HS210, was coated on a 185 μm thick transparent PET film subbed for gelatin in a dry thickness of 40 μm, and dried. Then, a microfilter (Fuji Photo Film Co., Ltd., FM300; porous spreading layer composed of cellulose triacetate) of a 3 μm mean pore size impregnated with 0.5% nonionic surfactant, HS210, was press-laminated thereon under swelling with moisture. 10 μl portions of blood samples of different Hb concentrations prepared in the same manner as in Example 1 were applied to the film while pressing onto the film 400-mesh nylon cloth.

About one minute after application of the blood samples, the reflective optical density of each spread blood was measured using a Macbeth RD514 reflection optical densitometer from the transparent PET film side. As is shown in Table 2, good correlation with the results obtained according to the standard process was confirmed.

TABLE 2

| Hb Concentration (g/dl) According to Standard Method | 4.4 | 9.0 | 13.2 | 16.8 | 21.9 |
|---|---|---|---|---|---|
| Reflective Optical Density | 0.71 | 0.82 | 0.99 | 1.10 | 1.26 |

While the invention has been described in detail and with reference to specific embodiments thereof, it will be apparent to one skilled in the art that various changes and modifications can be made therein without departing from the spirit and scope thereof.

What is claimed is:

1. A hemoglobin concentration-determining article comprising a water-impermeable support having integrally provided thereon, in sequence, a hydrophilic binder layer and a porous spreading layer which has a hydrophilic surface and in which the surface of the internal voids or the interior is hydrophilic and water-insoluble, said porous spreading layer being constituted so that an aqueous sample applied thereto can be spread and incorporated therein in a substantially definite volume per unit area, wherein the porous spreading layer comprises a non-fibrous porous material having a mean pore diameter of about 2.5 μm to about 500 μm or a fibrous porous material having a yarn number count of from about 40 to about 100.

2. The hemoglobin concentration-determining article as claimed in claim 1, wherein the non-fibrous porous material comprises a porous membrane.

3. The hemoglobin concentration-determining article as claimed in claim 2, wherein said fibrous porous material is glass fiber, a fabric or paper.

4. The hemoglobin concentration-determining article as claimed in claim 1, wherein said water-impermeable support is transparent and planar.

5. The hemoglobin concentration-determining article as claimed in claim 1, wherein said water-impermeable support is a planar support of glass or a synthetic resin film.

6. The hemoglobin concentration-determining article as claimed in claim 1, wherein said porous spreading layer contains one or more agents to stabilize the hue of hemoglobin or erythrocyte membrane-modifying agents selected from the group consisting of a pH buffer, an anticoagulant, an antihemolytic agent, an antioxidant, an oxidizing agent, a dye, a pigment, an inorganic salt, an aldehyde, an isocyanate and hydrogen peroxide.

7. The hemoglobin concentration-determining article as claimed in claim 1, wherein said hydrophilic binder layer is formed of a member selected from the group consisting of gelatin, agarose, dextran, polyvinyl alcohol, polyacrylamide and polyacrylic acid.

8. The hemoglobin concentration-determining article as claimed in claim 1, wherein said hydrophilic binder layer contains one or more additives selected from the group consisting of nonionic, cationic or anionic surfactants, plasticizers, inorganic salts, organic acid salts, pH buffers, pigments, dyes, solid fine particulate fibers, oxidizing agents, reducing agents, acids and alkalis.

9. The hemoglobin concentration-determining article as claimed in claim 1, wherein said hemoglobin concentration-determining article is free of any agents which elute therefrom upon contact with the aqueous sample to permit hemoglobin concentration determination.

10. The hemoglobin concentration-determining article as claimed in claim 6, wherein said porous spreading layer consists essentially of said non-fibrous porous material or said fibrous porous material and said additives.

11. The hemoglobin concentration-determining article as claimed in claim 1, wherein said non-fibrous porous material has a mean pore diameter of from about 3 μm to about 100 μm and wherein said fibrous porous material has a yarn number count of from about 60 to about 80.

* * * * *